US012797411B2

(12) United States Patent
Tornatore

(10) Patent No.: US 12,797,411 B2
(45) Date of Patent: Nov. 17, 2026

(54) REGENERATIVE $CO_2$ TREATMENT SYSTEM AND METHOD

(71) Applicant: Renee Tornatore, Corydon, IN (US)

(72) Inventor: Renee Tornatore, Corydon, IN (US)

( * ) Notice: Subject to any disclaimer, the term of this patent is extended or adjusted under 35 U.S.C. 154(b) by 708 days.

(21) Appl. No.: 17/572,025

(22) Filed: Jan. 10, 2022

(65) Prior Publication Data

US 2022/0125831 A1 Apr. 28, 2022

Related U.S. Application Data

(63) Continuation-in-part of application No. 16/924,873, filed on Jul. 9, 2020, now Pat. No. 12,616,717.

(60) Provisional application No. 63/135,958, filed on Jan. 11, 2021, provisional application No. 62/872,749, filed on Jul. 11, 2019.

(51) Int. Cl.

| | |
|---|---|
| ***A61K 9/00*** | (2006.01) |
| ***A61K 9/70*** | (2006.01) |
| ***A61K 33/00*** | (2006.01) |
| ***A61K 38/06*** | (2006.01) |
| ***A61K 45/06*** | (2006.01) |
| ***A61N 1/40*** | (2006.01) |
| ***A61P 17/14*** | (2006.01) |

(52) U.S. Cl.

CPC ............ *A61K 33/00* (2013.01); *A61K 9/0019* (2013.01); *A61K 9/7023* (2013.01); *A61K 38/063* (2013.01); *A61K 45/06* (2013.01); *A61N 1/40* (2013.01); *A61P 17/14* (2018.01)

(58) Field of Classification Search

CPC .. A61P 17/14; A61N 1/40; A61K 9/00; A61K 9/0019; A61K 9/0021

See application file for complete search history.

(56) References Cited

U.S. PATENT DOCUMENTS

| | | | | |
|---|---|---|---|---|
| 2004/0081642 A1* | 4/2004 | Loscalzo | A61K 31/355 424/94.1 |
| 2007/0016117 A1* | 1/2007 | Sliwa | A45D 26/00 30/32 |
| 2014/0271810 A1* | 9/2014 | Perricone | A61Q 7/00 424/450 |
| 2017/0246205 A1 | 8/2017 | Stasko et al. | |
| 2021/0008102 A1 | 1/2021 | Tornatore | |

FOREIGN PATENT DOCUMENTS

| | | | |
|---|---|---|---|
| JP | H08107936 A * | 4/1996 | A61N 1/40 |
| WO | 2014142970 | 9/2014 | |
| WO | WO-2014142970 A9 * | 8/2016 | A61M 5/3298 |

OTHER PUBLICATIONS

Homer Nazeran et al, Nanoscale Glutathione Patches Improve Organ Function, SBEC 2010, IFMBE Proceedings 32, pp. 134-137, 2010 (Year: 2010).*
Ilution Information System, Nitrogen Oxides (NOx), Air Pollution Information System, downloaded in Aug. 2024 (Year: 2024).*
Rafet Koca et al, Evaluation of lipid peroxidation, oxidant/antioxidant status, and serum nitric oxide levels in alopecia areata, Med Sci Monit, 2005; 11(6): CR296-299 (Year: 2005).*
JPH08107936A, Google English translation document, downloaded in May 2025 (Year: 2025).*
KJean (Rotator Cuff Surgery—4 weeks post-op, p. 8, Shoulder Problems, Forums, patient, publication date:2016 (Year: 2016).*
Research-Gate, "A simplified version of the mTOR signalling pathway," article (May 4, 2020) 14 pages, https://www.researchgate.net/figure/A-simplified-version-of . . . thway-MTORC1-received-and-integrates-the_fig1_257103989.
Levin, "Molecular Bioelectricity: how endogenous voltage potentials control cell behavior and instruct pattern regulation in vivo," article (Dec. 1, 2014) Molecular Biology of the Cell Perspective, vol. 25, pp. 3835-3850.
The American Society for Cell Biology, "Molecular Biology of the Cell Chart (MBoC)," article (Dec. 1, 2014) 2 pages, https://www.ncbi.nim.nih.gov/pmc/articles/PMC4244194/figure/F1/.
Kumar et al., "Hypoxia Inducible Factor pathway and Physiological Adaptation: A Cell Surbival Pathway?," article (Sep. 27, 2015) pp. 1-22, Department of Biotechnology, Konkuk University, https://www.ncbi.nim.nih.gov/pmc/articles/PMC4600544/.
Tyler, "Nature's Electric Potential: A Systematic Review of the Role of Bioelectricity in Wound Healing and Regenerative Processes in Animals, Humans, and Plants," article (Sep. 4, 2017) vol. 8, Article 627, 18 pages, Frontiers in Physiology, www.frontiersin.org.
Blanpain et al., "Epithelial Stem Cells: Turning over New Leaves," article (Feb. 9, 2007) 26 pages, https://www.ncbi.nlm.nih.gov/pmc/articles/PMC2408375/.
Ledford, "Electric switch could turn on limb regeneration," article (Feb. 28, 2007) 4 pages, https://www.nature.com/news/2007/070226/full/news070226-8.html.
Oliveira, et al., "Electrical stimulation shifts healing/scarring towards regeneration in a rat limb amputation model," article (Aug. 7, 2019) 14 pages, Scientific Reports, (2019)9:11433, https://doi.org/10.1038/s41598-19-47389-w.
Atala, et al., "Wound Healing Versus Regeneration: Role of the Tissue Environment in Regenerative Medicine," article (Jan. 1, 2011) 24 pages, Howard Hughes Medical Institute, https://www.ncbi.nlm.nih.gov/pmc/articles/PMC3826556/.
Tseng, et al., "Cracking the bioelectric code; Probing endogenous ionic controls of pattern formation," article (Jan./Feb. 2013) Communicative & Integrative Biology, vol. 6, Issue 1, p. 1-8, www.landesbioscience.com.
Choudhry, et al., "Advances in Hypoxia-Inducible Factor Biology," article (Feb. 6, 2018) Cell Metabolism 27, pp. 281-298, https://doi.org/10.1016/j.cmet.2017.10.005.
Preston, "Salamander's Genome Guards Secrets of limb Regrowth," article (Jul. 2, 2018) 13 pages, Developmental Biology, https://www.quantmagazine.org/axolotl-genome-slowly-yields-secrets-of-limb-regrowth-20180702/.

(Continued)

*Primary Examiner* — Micah Paul Young
(74) *Attorney, Agent, or Firm* — Amundsen Davis, LLC

(57) ABSTRACT

The present technology provides regenerative treatment methods and apparatus to stimulate hair growth. Regenerative treatments to stimulate hair growth include the subcutaneous application of carbon dioxide, and may also include suction, energy input, and topical application of nutrients to a patient's scalp. Regenerative treatment methods include an initial treatment phase and a maintenance treatment phase.

20 Claims, 6 Drawing Sheets

(56) References Cited

OTHER PUBLICATIONS

Paddock, "Study shows blood cells need nitric oxide to deliver oxygen," article (Apr. 13, 2015) 2 pages, Medical News Today, https://www.medicalnewstoday.com/articles/292292.php.

Wei, et al., "Roles of mTOR Signaling in Tissue Regeneration," article (Sep. 12, 2019) 25 pages, https://www.ncbi.nlm.nih.gov/articles/PMC6769890/.

Nagoba, "Role of Acid in Wound Healing," article (Apr. 30, 2020) 6 pages, https://www.woundresearch.com/article/acidic-environment-and-wound-healing-review.

Ultima Neuro, "Stimulator Info," article, (Jul. 22, 2015) 6 pages.

Buarque De Gusmao, et al., "Advanced Techniques in Bone Regeneration," article (Aug. 31, 2016) 19 pages, DOI: 10.5772/63745, https://www.intechopen.com/books/advanced-techniques-in-bon . . . ion/acoustic-therapy-as-mechanical-stimulation-of-osteogenesis.

Kumar et al., "Adult skin-derived precursor Schwann cells exhibit superior myelination and regeneration supportive properties compared to chronically denervated nerve-derived Schwann cells," article (2016) 2 pages, https://www.ncbi.hlm.nlh.gov/m/pubmed/26854934/?=4&/rom=/2440805/related.

Mclaughlin, et al., "Bioelectric signaling in regeneration: Mechanisms of ionic controls of growth and form," article (Dec. 25, 2017) 13 pages, Developmental Biology 433 (2018) 177-189, https://dx.doi.org/10.1016/j.ydbio.2017.08.032.

Zelenkova, "Carboxytherapy Non-Invasive Method in Dermatology and Some Other Branches of Medicine," article (Apr. 8, 2019) ACTA Scientific Medical Sciences, vol. 3, Issue 5, May 2019, pp. 42-48.

Sakai, et al., "A Novel System for Transcutaneous Application of Carbon Dioxide Causing an "Artificial Bohr Effect" in the Human Body," article (2011) 2 pages, Plos One, https://journals.plos.org/plosone/article?id=10.1371/journal.pone0024137.

Greijer AE, et al., "Up-regulation of gene expression by hypoxia is mediated predominantly by hypoxia-inducible factor 1 (HIF-1)," article (2005) 2 pages, https://www.ncbi.nlm.nih.gov/m/pubmed/15906272/.

Apec Water, Free Carbon Dioxide in Water, downloaded in Sep. 2021 (Year: 2021).

Pietro Romeo, Extracorporeal Shock Wave Therapy in Musculoskeletal Disorders: A Review, Med Princ Pract 2014;23:7-13 (Year: 2014).

Luther C. Kloth, Electrical Stimulation Technologies for Wound Healing, Advances in Wound Care, vol. 3, No. 2, 2014 (Year : 2014).

Alu Bohuslays'kyi, Effect of nitric oxide on the efficiency of oxygen consumption by the working skeletal muscle in fatigue]. Fiziol Zh. 2005;51(1):33-42. Ukrainian. PMID: 15801198 (Year: 2005).

Li et al., "Exposure to 50 Hz electromagnetic fields enhances hair follicle regrowth in C57BL/6 mice" article (2019) Experimental Biology and Medicine (Maywood) 244(5): pp. 389-394, https://www.ncbi.nlm.nih.gov/pmc/articles/PMC6488868/.

Schleip et al., "Fascia Is Able to Actively Contract and May Thereby Influence Musculoskeletal Dynamics: A Histochemical and Mechanographic Investigation | Physiology" article (2019) Frontiers in Physiology, pp. 1-15 https://doi.org/10.3389/fphys.2019.00336.

Stem-Rim, "What is Regeneration-inducing Medicine?," article (2022) 3 pages, https://stemrim.com/english/about/theirs/.

Uppsala University, "Nitric oxide a possible treatment for COVID-19, study finds," article (2020) 3 pages, https://www.sciencedaily.com/releases/2020/10/201002111724.htm.

Tejero et al., "Sources of Vascular Nitric Oxide and Reactive Oxygen Species and Their Regulation," article (2018) Physiol Rev 99: pp. 311-379, https://journals.physiology.org/doi/pdf/10.1152/physrev.00036.2017.

TMD—Occlusion, "Hair Loss: The Real Underlying Causes Are Not Androgenetic," article (2020) 14 pages, https://tmdocclusion.com/home/connection-to-other-diseases-and-syndromes/hair-loss/.

Tellez-Segura, "Involvement of Mechanical Stress in Androgenetic Alopecia," article (2015) International Journal of Trichology: 7(3), PMC4639964, pp. 95-99, https://www.ncbi.nlm.nih.gov/pmc/articles/PMC4639964/.

Gao et al., "Correlation between cervical lordosis and cervical disc hern . . . : Medicine," article (2019) Medicine: vol. 98, Issue 31, pp. 1-6, https://journals.lww.com/md-journal/fulltext/2019/08020/correlation_between_cervical_lordosis_and_cervical. 15.aspx.

Shin et al., "Temporal Trends in Cervical Spine Curvature of South Korean Adults Assessed by Deep Learning System Segmentation, 2006-2018," article (Oct. 15, 2020) pp. 1-13, JAMA Network Open, https://jamanetwork.com/journals/jamanetworkopen/fullarticle/2771734.

* cited by examiner

REGENERATIVE $CO_2$ TREATMENT SYSTEM AND METHOD

RELATED APPLICATIONS

This application claims the benefit of U.S. Provisional Application No. 63/135,958, filed on Jan. 11, 2021, and is a continuation-in-part of U.S. application Ser. No. 16/924,873, filed Jul. 9, 2020, currently pending, which claims the benefit of U.S. Provisional Application No. 62/872,749, entitled "CO2 Treatment Apparatus and Method," filed Jul. 11, 2019. The disclosures of each of the foregoing are hereby incorporated by reference in its entirety.

FIELD OF THE INVENTION

The present technology relates to the use of carbon dioxide ($CO_2$) for regenerative therapeutic purposes, and provides certain methods of regeneration treatment, as well as devices for implementing treatment and for the delivery of carbon dioxide to targeted body tissues. In particular, the present technology relates to regenerative treatment systems and methods for stimulating hair growth on the head of a patient.

BACKGROUND

The regeneration of damaged biological tissues is of significant interest. Regeneration is distinguishable from processes of scarring and healing, and regenerative medicine focuses on ways to optimize tissue regeneration by inducing the body's ability to regenerate. Various strategies have been developed for regenerative treatments to promote tissue regeneration, including for example, the use of biomaterials as scaffolds, cells, and combinations of biomaterials and cells.

Many studies have been conducted in both plants and animals to try to understand how regenerative processes work. For example, as described in "Nature's Electric Potential: A systematic Review of the Role of Bioelectricity in Wound Healing and Regenerative Process in Animals, Humans, and Plants, from the Frontiers in Physiology," Shena E. B. Tyler (Frontiers in Physiology, Sep. 4, 2017), regenerative processes can be broken down into five phases.

In the first phase, there is an injury (wound), or disruption to the tissue cells, such as by 1) spatial variations in ion channels or pumps, or 2) disruption in gap junctions. This creates extracellular ionic current flow, and established voltage gradients. This essentially creates a bioelectric voltage gradient. Bioelectricity is the flow of current carried by mobile charged ions, across cell membrane and along exterior and interior ionic environments of cells. The body then responds by initiating processes to either regenerate or scar and repair.

In the second phase, changes in polarity are communicated. The signals may be carried via: Electrical Fields—presence of dipole with no immediate barrier; Membrane potential—presence of dipole across barrier with selective permeability created by ion gradients across a membrane via action of ion channels and pumps; Flux—flow of ions through channels or pumps per unit of time; PH gradients—by proton pumps to modify H+ gradients. The article "Bioelectric Signaling in Regeneration: Mechanisms of Ionic Controls of Growth and Form," McLaughlin et al., (Developmental Biology 433 (2018)), explains that transmembrane potentials, fluxes of individual ions, and iso-electric cell compartments that are established by gap junctions, convey information to at least target cells. Further, as described in the article "Molecular Bioelectricity: How Endogenous Voltage Potentials Control Cell Behavior And Instruct Pattern Regulation in Vivo," Michael Levin (Molecular Biology of the Cell, Dec. 1, 2014), it is believed that this signaling modality is used to process and transmit information about regenerative parameters such as cell type, tissue size, positional information, axial polarity, and organ identity.

The third phase involves mechanisms acting as receptors for the signals, such as proton pumps and other cells. Biophysical transduction mechanisms may include: 1) Voltage sensing domain, 2) loss of intracellular K+, Electroosmosis 4) Voltage gating of signaling molecular transport, 5) Ca++ influx, 6). Secondary response, amplification, transcriptional effectors may include: 1) integrin, 2) Slug/Sox10, 3) Notch, 4) NF-kB, 5) PTEN.

The fourth phase includes ionic flux, which involves the downstream activation of a number of gene responses, which evoke transcriptional cascades involved in the control of morphologies and regeneration.

The fifth phase involves initiating a cascade of events through cellular death and proliferation, and differentiation of stem cells to regenerate parts, pieces, or entire modules. It is believed that when bioelectric patterns are specifically disrupted, predictable and coherent changes in morphogenesis occur. It is also believed that the necessary parameter is voltage potential, without regard necessarily to any one channel gene (which could have had scaffold or binding roles) or even any one ion type (which could have had chemical, not electrical, roles). Accordingly, achieving the correct voltage in the target biological tissue may trigger the regenerative cascade to regenerate parts, pieces, or entire modules.

Various treatments and methodologies have been developed to try to improve physical and aesthetic properties of human tissues over the years. One example is the subcutaneous application of carbon dioxide, which is known as carboxytherapy. Typically, carboxytherapy uses a series of small injections with a thin needle attached to a tube which delivers tiny quantities of medical grade carbon dioxide below the skin's surface in a controlled flow and dose via a specially designed machine.

Carbon dioxide acts as a signal for poor blood circulation in the body. For example, when a human inhales, they breathe in oxygen into the lungs, and red blood cells pick up that oxygen and carry it to tissues in the body. Tissue cells within the body release carbon dioxide as their waste product. When blood cells encounter high concentrations of carbon dioxide, they release oxygen molecules they are carrying and pick up the carbon dioxide, carrying it back to the lungs to be exhaled. The article "Carboxytherapy Non-Invasive Method in Dermatology and Some other Branches of Medicine," Zelenkova (ATCA 3:5 2019) describes carboxytherapy and effects it has on the human body, including the Bohr effect and that an increase in blood $CO_2$ concentration leads to a decrease in blood pH, which will result in hemoglobin proteins releasing their load of oxygen, while, conversely a decrease in blood $CO_2$ provokes an increase in pH, which results in hemoglobin picking up more oxygen.

It has been found that when small amounts of carbon dioxide gas are injected just below the surface of the skin, the body reacts by increasing the blood circulation to that area. Studies have demonstrated that carboxytherapy improves skin elasticity, improves circulation, encourages collagen repair, improves the appearance of fine lines and wrinkles, and destroys localized fatty deposits. The most common aesthetic indications for treatment with carboxytherapy are for cellulite and localized fat reduction, stretch marks (striae), acne scars, skin laxity and wrinkle reduction.

However, carboxytherapy alone is not truly a regenerative treatment. It is believed that carboxytherapy alone does not utilize all five phases of the regenerative processes discussed above. Accordingly, it is desirable to provide improved regenerative treatments.

SUMMARY OF THE INVENTION

The present technology provides regenerative treatment methods and systems that use subcutaneous carbon dioxide as one aspect in stimulating hair growth.

In one example, a regenerative treatment method for stimulating hair growth is provided that includes conducting an initial treatment phase and a maintenance treatment phase. The initial treatment phase includes at least one initial phase therapy session and at least one initial phase personal administration. Each initial phase therapy session includes at least subcutaneously applying carbon dioxide in at least one location on a scalp of a patient, and each initial phase personal administration includes at least application of a high frequency device to the scalp. The maintenance treatment phase is conducted after the initial treatment phase. The maintenance treatment phase includes at least one maintenance phase therapy session and at least one maintenance phase personal administration. Each maintenance phase therapy session includes at least subcutaneously applying carbon dioxide in at least one location on the scalp of the patient, and each maintenance phase personal administration includes at least at least application of a high frequency device to the scalp.

In another example, a regenerative treatment kit for use during personal administration sessions of a regenerative treatment therapy to stimulate of hair growth is provided. The regenerative treatment kit includes: a high frequency device; a first patch configured to be applied to a patient's skin, the first patch including glutathione; and nitric oxide. The regenerative treatment kit may also include a second patch configured to be applied to a patient's skin, the second patch including a plurality of vitamins. The regenerative treatment kit may further include at least one of a posture wedge pillow and/or a posture shoulder strap.

BRIEF DESCRIPTION OF THE DRAWINGS

Specific examples have been chosen for purposes of illustration and description, and are shown in the accompanying drawings, forming a part of the specification. Like components within the drawings are given the same reference numbers.

DETAILED DESCRIPTION

Regenerative systems and treatment methods of the present technology may be used to treat biological tissue damage and/or deterioration in a patient's scalp and stimulate hair growth. Generally, poor circulation of blood tends to result in a poor supply of oxygen to bodily tissues, which leads to deterioration of bodily tissues, since such tissues rely upon oxygen to remain intact and healthy. When body tissues are stressed or damaged, they often experience inflammation. Repeated inflammation over time can cause a buildup of scar tissue and adhesion, which is poorly vascularized. Lack of blood flow to poorly vascularized areas can cause deterioration of and further damage to the biological tissue. When such damage occurs in the human scalp, hair follicles no longer produce hair and baldness can result.

Regenerative treatments methods of the present technology may be used to treat damage to the fascia of the scalp, including the hair follicles.

Regenerative treatment methods of the present technology include subcutaneous applications of carbon dioxide. The subcutaneous application of carbon dioxide is administered during therapy sessions, in a clinical setting. Regenerative treatment methods of the present technology also include inducement of ionic flux, such as by using a high frequency ozone producing device, and may include topical application of nutrients to a patient's scalp. Various steps of the regenerative treatment methods of the present technology may be administered in a clinical setting during therapy sessions, or may be self-administered by the patient or a caregiver during a personal administration session.

Figure 1:
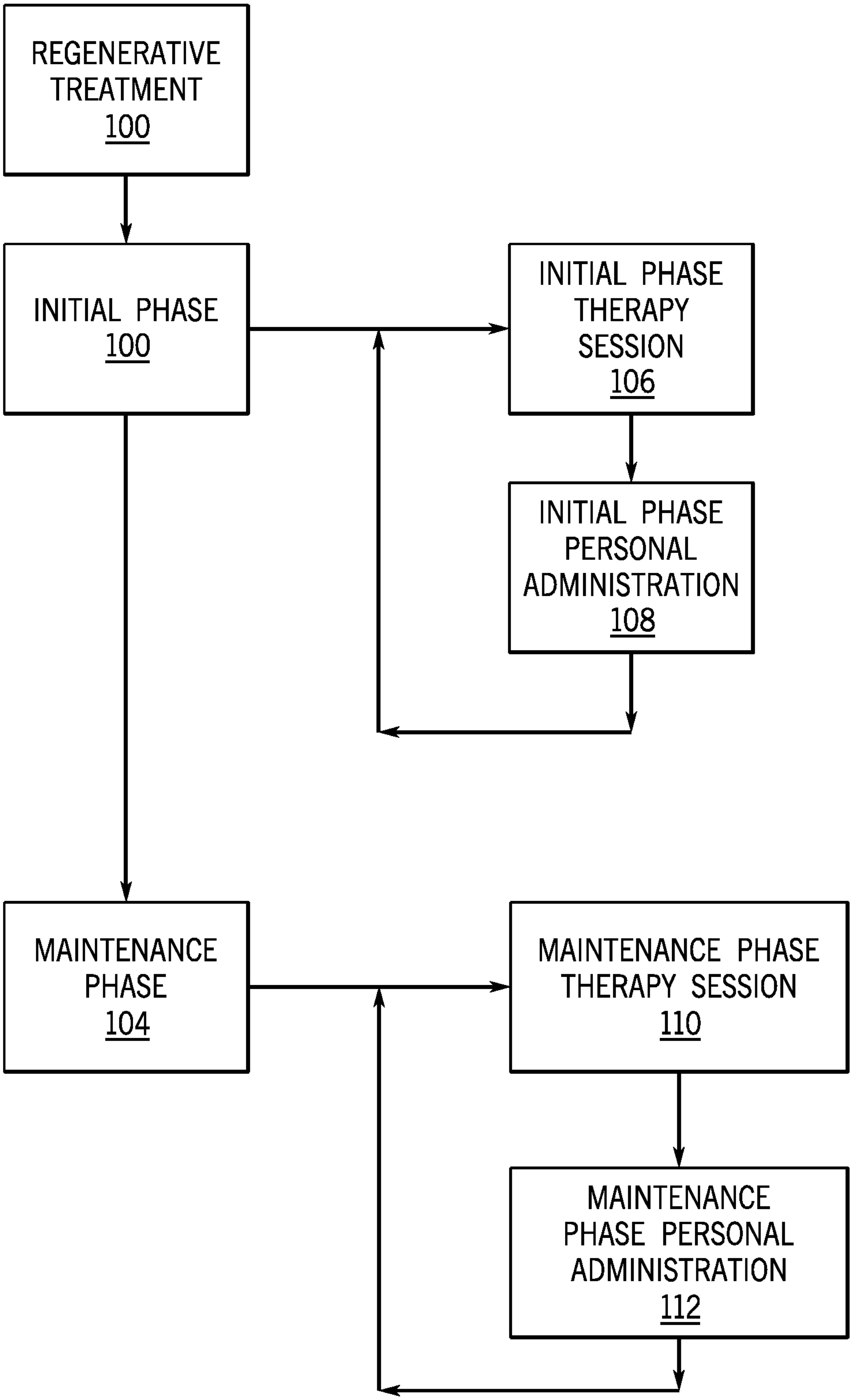
FIG. 1 is a flow chart illustrating one example of a regenerative treatment method of the present technology.

As shown in FIG. 1, a regenerative treatment method 100 of the present technology includes two treatment phases: an initial treatment phase at step 102, and a maintenance treatment phase at step 104. Generally, the initial treatment phase 102 includes at least one initial phase therapy session at step 106, and may also include at least one initial phase personal administration session at step 108. The initial phase 102 generally includes a pre-determined number of repetitions of at least step 106, and thus a pre-determined number of initial phase therapy sessions. The initial phase therapy sessions at step 106 tend to be administered in relatively close proximity in time, and are intended to regenerate target biological tissue and stimulate hair growth. The initial phase 102 also generally includes a plurality of initial phase personal administrations at step 108. Steps 106 and 108 may be carried out in succession and that succession may be repeated a set number of times. Alternatively, during the initial phase 102, either of initial phase therapy session at step 106 or the initial phase personal administrations at step 108 may be repeated prior to any further occurrence of the other step. Preferably, the initial phase 102 includes at least one initial phase therapy session at step 106, and also includes at least one initial phase personal administration session at step 108 that occurs after the at least one initial phase therapy session at step 106. In at least some examples, the initial phase personal administration session at step 108 may be repeated multiple times between each initial phase therapy session at step 106.

The maintenance phase at step 104 includes at least one maintenance phase therapy session at step 110, and may also include at least one maintenance phase personal administration 112, as well as repetitions of each step as desired or recommended. The repetitions of step 110 maintenance phase therapy session may be spaced father apart in time than the initial phase therapy sessions at step 106, and are intended to at least maintain the level of regeneration achieved during the initial treatment phase at step 102. The number of maintenance phase therapy sessions 110 may be indefinite, and may be periodic continuously for any suitable period of time, up to and including the lifetime of the patient.

Steps 110 and 112 may be carried out in succession and that succession may be repeated a set number of times. Alternatively, during the maintenance phase 104, either of maintenance phase therapy session at step 110 or the maintenance phase personal administrations at step 112 may be repeated prior to any further occurrence of the other step. Preferably, the maintenance phase 104 includes at least one maintenance phase therapy session at step 110, and also includes at least one maintenance phase personal administration session at step 112 that occurs after the at least one maintenance phase therapy session at step 112. In at least some examples, the maintenance phase personal administration sessions at step 112 may be repeated multiple times between each maintenance phase therapy session at step 110.

The number of initial phase therapy sessions 106 may vary from patient to patient, or based upon the type regenerative treatment. For regenerative treatment of the scalp to stimulate hair growth, the number of initial phase therapy sessions 106 may be any suitable number of therapy sessions, such as from ten to twenty initial therapy sessions. The number of initial phase therapy sessions may vary depending upon the severity and duration of the patient's balding. In some instances, the number of initial phase therapy sessions 106 may be less than ten, or greater than twenty. In other instances, the number of initial phase therapy sessions 106 may be about twenty, or between about ten and about twenty, such as from about twelve to about fifteen, from about fifteen to about twenty, or from about twenty to about twenty five. In some examples, the number of initial phase therapy sessions 106 may be ten, eleven, twelve, thirteen, fourteen, fifteen, sixteen, seventeen, eighteen, nineteen, twenty, twenty-one, twenty-two, or twenty five.

The frequency of initial phase therapy sessions 106 may also vary from patient to patient, or based upon the type regenerative treatment. For regenerative treatment of the scalp to stimulate hair growth, during the initial treatment phase 102, initial phase therapy sessions 106 are preferably scheduled to occur about once per week, or about once every seven to ten days. For example, in some cases, initial phase therapy sessions 106 may occur once every seven to ten days for twenty visits.

The maintenance phase 104 of regenerative treatment method 100 is intended to occur after the initial phase 102. The maintenance phase 104 may include maintenance phase therapy sessions at step 110, which may be spaced apart over a greater periods of time than the initial phase therapy sessions at step 106. For example, for hair regrowth regenerative treatments during the maintenance phase 104, the step of a maintenance phase therapy session 110 may be performed once per month, once every two months, or once every three months. In addition, or alternatively, to therapy sessions, the maintenance phase 104 may include maintenance phase personal administration sessions at step 112. Maintenance phase personal administration at step 112 may occur more frequently than therapy sessions 110 during the maintenance phase 104, such as once per week, or even as needed.

Figure 2:
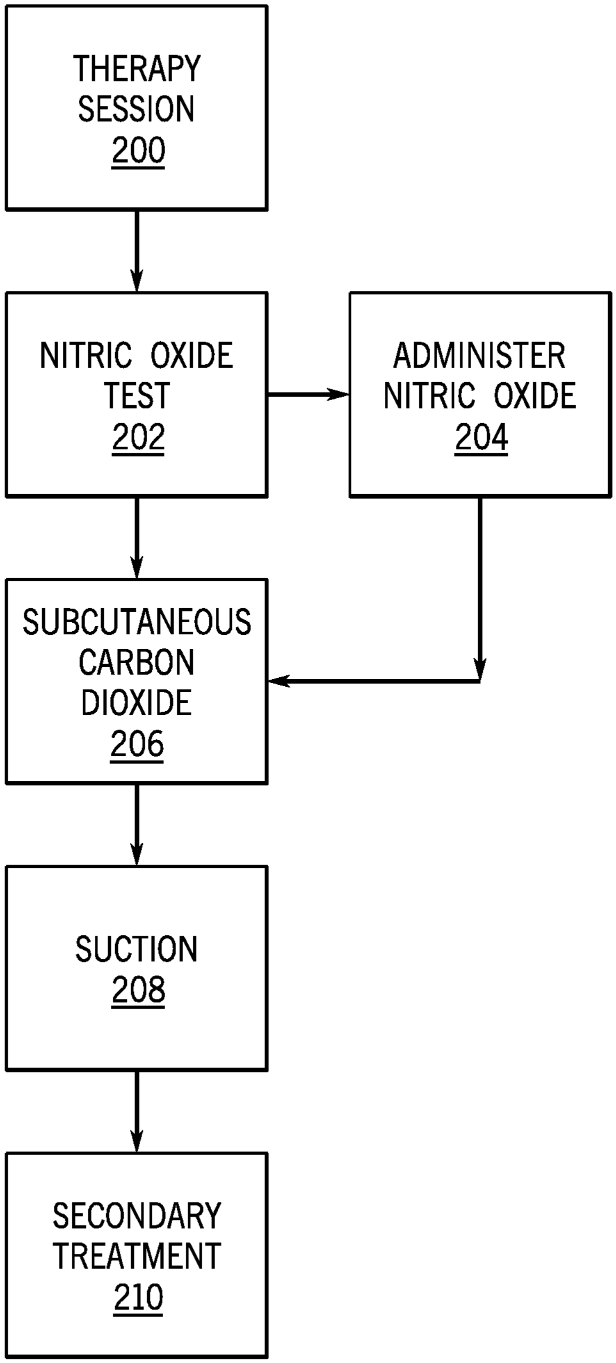
FIG. 2 is a flow chart illustrating on example of a therapy session of the regenerative treatment method of FIG. 1.

FIG. 2 illustrates one example of a therapy session 200 of the present technology, which may be an initial phase therapy session 106 or a maintenance phase therapy session 110.

Each therapy session 200 of the present technology includes subcutaneously applying carbon dioxide in at least one location on the scalp of the patient at step 206. Subcutaneous application of carbon dioxide is administered by a clinician, and the carbon dioxide is injected in at least one location within the target area. In regenerative treatments to stimulate hair growth, subcutaneously applying carbon dioxide includes injecting carbon dioxide into the patient's scalp, into the subcutaneous tissue underneath the epidermis and dermis. The carbon dioxide may be injected in at least one location, or at multiple locations on the patient's scalp. In examples where subcutaneously applying carbon dioxide includes injecting carbon dioxide at multiple locations on the patient's scalp, the injections may be placed in a spaced pattern. One example of a spaced pattern that may be used is a grid. The configuration of the spaced pattern may vary as the regenerative treatment progresses. In some examples, such as during the first few initial phase therapy sessions, a closer spaced pattern, such as a grid with injection points being about one inch apart, may be used. Over time, fewer injections may be needed, and the spaced pattern may include wider spacing, such as two injections per quadrant of a patient's scalp.

Without being bound by any particular theory, injection of carbon dioxide is believed to provide many benefits, including potentially ripping scar tissue, stimulating blood flow, and promoting collagen formation. Injection of carbon dioxide may create a positive electrical event, and the carbon dioxide may disrupt all cells in the whole plane into which it is injected, causing an ionic gradient from resting to positive. With reference to phase 1 of the regenerative processes discussed above, injection of carbon dioxide may cause injury of cells so that the target biological tissue can regenerate new cells. Injection of carbon dioxide may initiate a downstream cascade of events via HIF (hypoxia induced factor) via the mTOR pathway as well as other pathways. With reference to phase 2 of the regenerative processes discussed above, injection of carbon dioxide may cause changes in the gap junction, which may initiate electrical field and membrane potential changes. Injection of carbon dioxide may also induce ionic flux and PH gradient changes due to the H+ characteristic of the $CO_2$ molecules in the carbon dioxide gas.

As an optional step, therapy session 200 may include administering a nitric oxide test at step 202, to assess the patient's nitric oxide level. Administration of the nitric oxide test may occur as one of the first procedures during a therapy session, such as prior to subcutaneously applying carbon dioxide at step 206. A nitric oxide test may include measurement of a patient's salivary nitrite, such as by applying the patient's saliva onto a nitric oxide test strip. Several types of nitric oxide test strips are commercially available for general use, and are designed to measure the amount of nitric oxide that is recirculated through the patient's saliva. While not being bound by any particular theory, the measurement is believed to be representative of the bioavailability of nitric oxide in the patient's body, and that having sufficient levels of nitric oxide within a patient's body promotes healing in the skin and other tissues. With at least some known nitric oxide test strips, when saliva is applied to the correct area on the test strip, color coded results appear that indicate whether a patient has sufficient levels of nitric oxide. If a patient is determined to have low levels of nitric oxide, based on the results indicated by the nitric oxide test strip, therapy session 200 may include administration of nitric oxide at step 204. Nitric oxide can be administered orally, and may be in the form of a tablet or capsule.

Each therapy session 200 may also include steps that are intended to cause or promote the third, fourth, and fifth phases of the regenerative process described above. Without being bound by any particular theory, it is believed that the subcutaneous application of carbon dioxide causes a wound, and initiates the first and second phases of the regenerative process. The carbon dioxide also serves as an anti-inflammatory, which may reduce the likelihood that the body will produce scar tissue, and thus facilitate the promotion of tissue regeneration. Regenerative treatments of the present technology take advantage of the presence of the subcutaneous carbon dioxide, and use the additional therapy steps described below to promote tissue regeneration.

For example, regenerative treatments to stimulate hair growth may include applying suction to the scalp at step 208. Suction may be performed using a suction device. Suction devices for applying suction to a patient's skin for various purposes are commercially available. Use of a suction device in regenerative treatments of the present technology, by applying suction to the scalp at step 208, after subcutaneously applying carbon dioxide at step 206, may pull the subcutaneously injected carbon dioxide up through the skin layers of the scalp up to the epidermis, and may break up adhesion.

Additionally, each therapy session 200 of the present technology may include applying at least one secondary treatment to the target area at step 210. Examples of secondary treatments for use in regenerative treatments to stimulate hair growth include, for example, applying energy input and/or applying nutrients topically to the scalp. Secondary treatment performed at step 210 can be performed during a therapy session after applying subcutaneous carbon dioxide at step 206, and can also be performed after applying suction to the scalp at step 208.

Without being bound by any particular theory, secondary treatments of the present technology may cause or promote ionic flux, and flipping positive and negative polarities within the target biological tissue. Either alone, or in combination with application of carbon dioxide to the target area at step 206, secondary treatment at step 210 may trigger a regenerative cascade within the target biological tissue.

Figure 3:
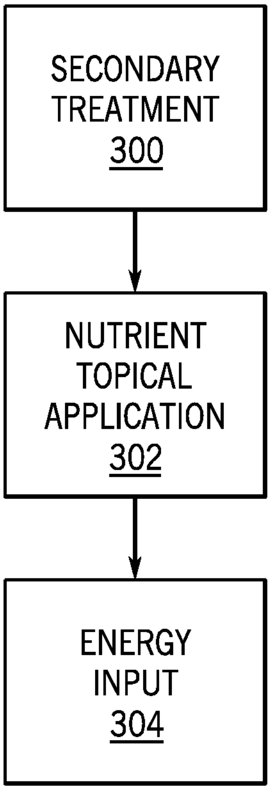
FIG. 3 is a flow chart illustrating on example of a secondary treatment of FIG. 2.

FIG. 3 shows one example of a secondary treatment 300 that may be used as a secondary treatment at step 210 during a therapy session 200, such as an initial phase therapy session 106 or a maintenance phase therapy session 110.

Secondary treatment 300 may include at least applying nutrients topically onto the scalp at step 302. The nutrients may include a combination of nutrients. The nutrients may be in a in the form of a nutrient mixture, and may be contained within a carrier fluid such as a liquid or gel. Applying nutrients topically onto the scalp at step 302 may include applying the nutrient mixture to the scalp and rubbing the nutrient mixture into the scalp.

Secondary treatment 300 may further include applying energy input at step 304. In some examples, energy input may be applied after applying subcutaneous carbon dioxide at step 206. In other examples, energy input may be applied after applying suction at step 208. Further, energy input may be applied after applying nutrients topically onto the scalp at step 302.

Energy input may be applied in various ways, depending upon the desired clinical outcome and status of the tissues in a patient's scalp, such as the severity of the baldness. For example, energy input may be applied in the form of an electrical current or electromagnetic pulse, or near infrared (NIR) light therapy. Various devices for applying electrical current and electromagnetic pulses, and for conducting NIR light therapy are known. Without being bound by any particular theory, it is believed that applying energy input induces ionic flux and promotes electroporation. Electroporation is a technique in which an electrical field is applied to increase the permeability of cells within the target tissue.

In examples where the a patient's baldness is not severely advanced, energy input may be applied during a therapy session 200 by using a high frequency device. High frequency devices are known for use in facial treatment, such as to reduce acne or wrinkles.

In examples where a patient's baldness is moderately advanced, energy input may be applied during a therapy session 200 by using NIR light therapy. Light is a form electromagnetic radiation characterized by particle- and wave-like properties. NIR light therapy uses directional low-power but high-fluency light, monochromatic or quasi-monochromatic, from lasers or light-emitting diodes (LEDs) usually in the wavelengths from about 600 nm to about 1000 nm). NIR light therapy devices of various types are known, and often includes a panel or grid of LEDs that emit light in the near infrared spectrum. NIR light therapy includes using an NIR light therapy device to apply near infrared light to the target tissue, such as the patient's scalp.

In examples where a patient's baldness is severely advanced, energy input may be applied during a therapy session 200 by applying electrical current, such as by generating electromagnetic pulses directed to penetrate the target tissue, such as the patient's scalp. Examples of treatments using electromagnetic pulses are pulsed shortwave (PSWT) therapy and pulsed electromagnetic diathermy. Various devices suitable for generating electromagnetic pulses directed to penetrate the target tissue are known. One example is the ActiPtach® device, available from BioElectronics Corporation. The device has an antenna and functions to produce a 27 MHz electromagnetic field 1000 times per second. When the antenna is placed over the target tissue, energy from the antenna is transferred into the target tissue as a localized therapy within the area covered by the antenna. Electromagnetic fields of from about 25 MHz to about 27 Mhz can be used to applying electrical current during energy input at step 304 in secondary treatments of the present technology for severely advanced baldness.

Referring back to FIG. 1, the initial phase personal administration at step 108 and the maintenance phase personal administration at step 112 may each also include applying a high frequency device on the patient's scalp. The patient, or a caretaker, may use a high frequency device on a patient's scalp during each personal administration step. During the initial phase personal administration at step 108, the patient, or a caretaker, may use a high frequency device on a patient's scalp multiple times per week, such as daily. During the maintenance phase personal administration at step 112, the patient, or a caretaker, may use a high frequency device at least about once per week.

Figure 4:
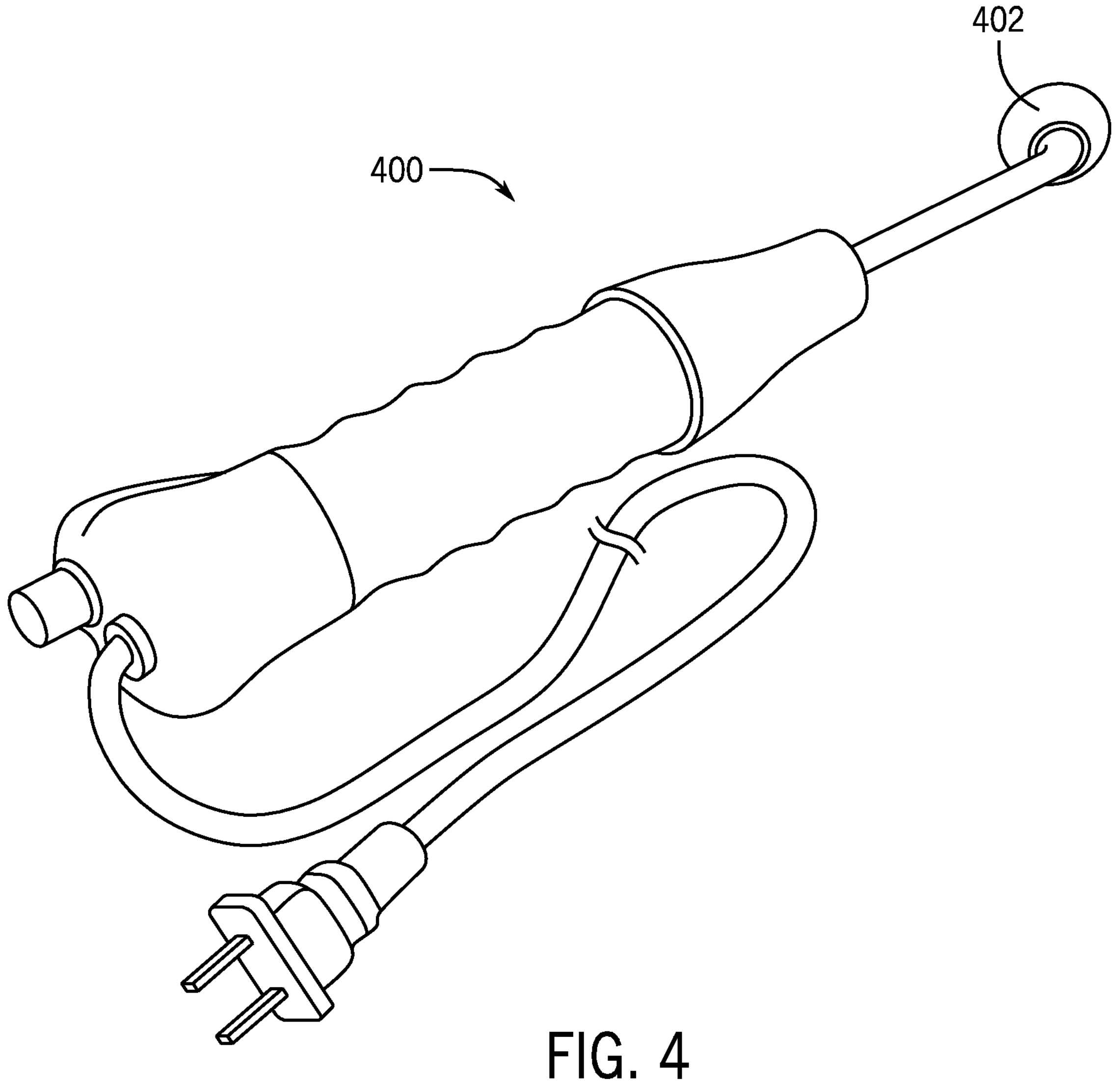
FIG. 4 illustrates one example of a high frequency device of the present technology.

FIG. 4 illustrates one example of a high frequency device 400 that may be used in regenerative treatments of the present technology, such as during an energy input step 304 of a secondary treatment 300 during a therapy session 200, or during an energy input step 608 during a personal administration session 600. High frequency device 400 includes an argon gas electrode 402 that emit a small electrical current and generates oxygen, specifically ozone, when applied to the patient's skin. In regenerative treatments of the present technology, the frequency of the high frequency device may be at or about 50 Hertz, such as from about 50 Hertz to 60 Hertz. The high frequency device may be applied over a desired time period. The time period may be about five minutes, at least five minutes, or any other suitable amount of time, such as between three minutes and ten minutes.

Figure 5:
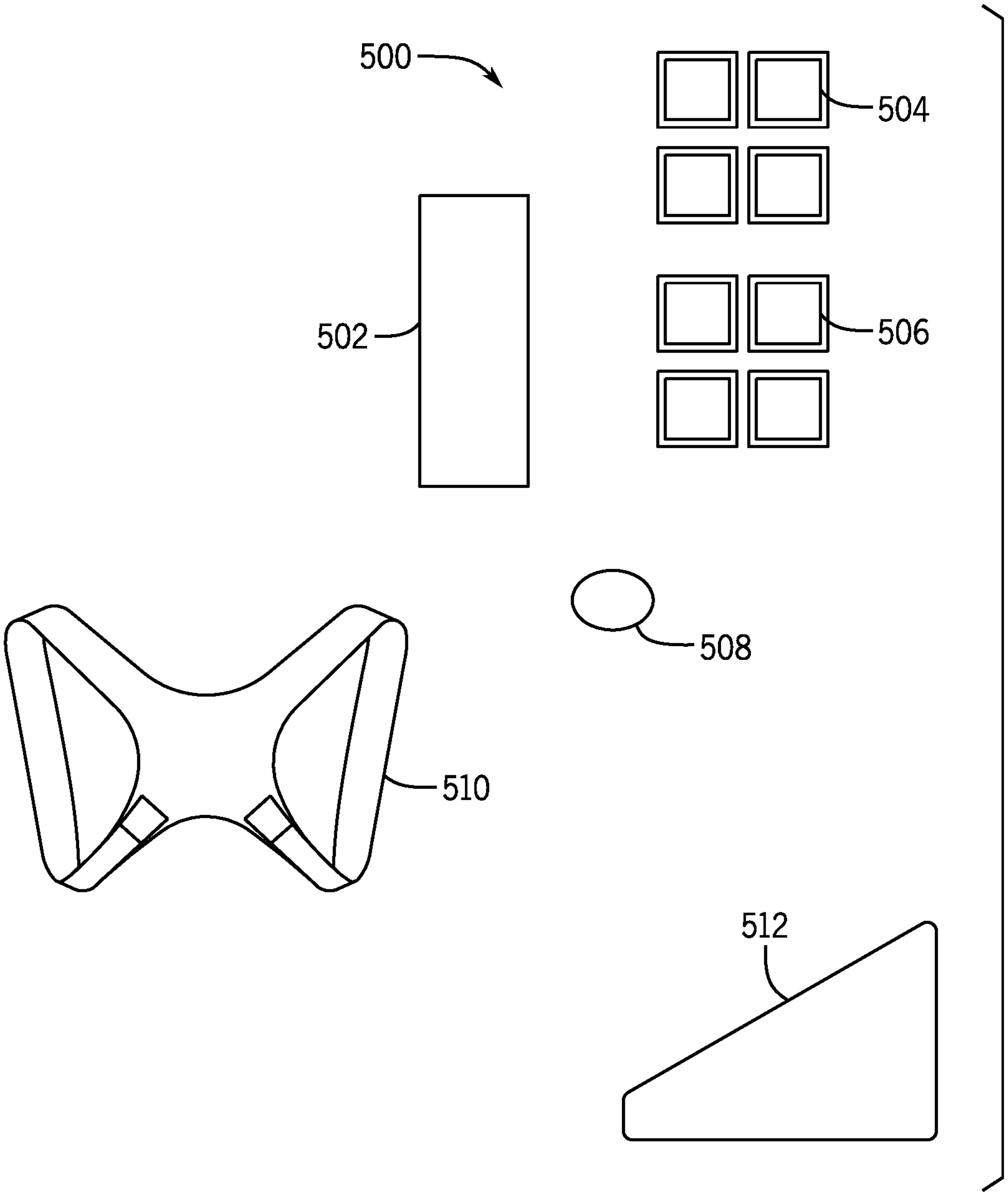
FIG. 5 illustrates one example of a regenerative treatment kit of the present technology.
Figure 6:
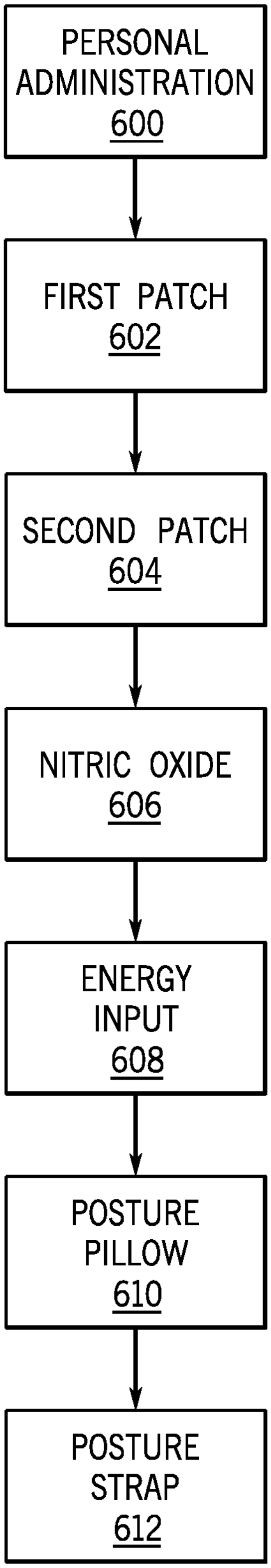
FIG. 6 is a flow chart illustrating on example of a personal administration method of the present technology.

Referring to FIGS. 5 and 6, a regenerative treatment kit 500 for use during a personal administration session of a regenerative treatment therapy to stimulate of hair growth, and a method 600 of conducting a personal administration session are shown.

The regenerative treatment kit 500 includes a high frequency device 502, at least one a first patch 504, at least one second patch 506, and nitric oxide 508. The high frequency device 502 may be configured to operate at 50 Hertz. The first patch 504 may be configured to be applied to a patient's skin, and may include glutathione. The regenerative treatment kit 500 kit may include a plurality of first patches. The second patch 506 may be configured to be applied to a patient's skin, and may include a plurality of vitamins. The regenerative treatment kit 500 kit may include a plurality of second patches. The nitric oxide 508 may be in a form to be taken orally. The regenerative treatment kit 500 may also include one or more posture improvement devices, such as a posture shoulder strap 510 and a posture wedge pillow 512. Posture shoulder strap 510 has two straps, each of which is configured as a loop through which a patient's arm can be inserted. The posture shoulder strap 510 also includes a connector, configured to connect the two straps and rest on the patient's back. The posture wedge pillow 512 has a wedge shaped profile, and a cut-out or dip in the center of the top edge. The posture wedge pillow 512 is configured to be used with a patient laying down with the high edge towards the patient and the patient's neck resting in the cut-out or dip.

One example of a method 600 of conducting a personal administration session is shown in FIG. 6. The steps of the method may be performed in any order, and certain steps may be performed for different durations or one or more times before another step is performed. The method 600 may include administering a first patch to skin of a patient at step 602. Such administration may cause the first patch to deliver glutathione to the patient. The method 600 of conducting a personal administration session may also include administering a second patch to the skin of the patient at step 604. Such administration may cause the second patch to deliver a plurality of vitamins to the patient. In some examples, the method 600 of conducting a personal administration session may include administering nitric oxide to the patient at step 606. The method 600 of conducting a personal administration session may further include applying energy input by application of the high frequency device 400 to the patient's scalp at step 608. In regenerative treatments of the present technology, the high frequency application may be conducted at 50 Hertz over a desired time period. The time period may be about five minutes, at least five minutes, or any other suitable amount of time, such as between three minutes and ten minutes.

The method 600 of conducting a personal administration session may also include one or more posture improvement steps. As shown in FIG. 6, step 610 includes using a posture pillow, such as posture pillow wedge 512. The step 610 of using the posture pillow may include a patient laying down and resting their head on the pillow for a period of at least about 10 minutes. The step 610 of using the posture pillow may be performed daily. As shown in FIG. 6, step 612 includes using a posture shoulder strap, such as posture shoulder strap 510. The step 612 of using a posture shoulder strap may be performed daily, and the posture shoulder strap may be used for any desired period of time, such as for up to about 8-12 hours per day.

EXAMPLES

The treatment method described herein is exemplary and it should be understood that the present technology encompasses, but is not limited to, the specific examples provided.

A. Hair Growth Stimulation

One example of a treatment method of the present technology is directed to the treatment of the scalp of a patient to stimulate hair growth. The initial treatment phase includes multiple initial phase therapy sessions, for example a total of twenty therapy sessions, where the therapy sessions are scheduled once or twice per week over a period of ten weeks.

Each initial phase therapy session includes subcutaneous application of carbon dioxide to the scalp of the patient. Prior to the subcutaneous application of carbon dioxide, the patient's nitric oxide level may be tested, and nitric oxide may be administered.

Subcutaneous application of carbon dioxide includes a plurality of injections of carbon dioxide in a grid pattern on the patient's scalp.

After the subcutaneous application of carbon dioxide, the clinician or a clinician's assistant applies suction to the patient's scalp using a suction device.

After the suction, nutrients are topically applied to the scalp and are physically rubbed into the scalp.

As a final step during the initial phase therapy session, an energy input step is performed. In one example, a high frequency device is used to apply electrical current to the scalp at 50 Hertz for a period of time from about 5 minutes to about 10 minutes. In an alternative example, an NIR therapy device is used to apply near infrared light to the patient's scalp for a period of time from about 5 minutes to about 10 minutes. In another alternative example, a device that generates electromagnetic pulses is used to direct electromagnetic pulses to penetrate the patient's scalp for a period of time from about 5 minutes to about 10 minutes.

During the time period between scheduled initial phase therapy sessions, the clinician may instruct the patient to self-administer one or more high frequency device applications. For example, the patient may self-administer the high frequency device once daily on days when a therapy session is not scheduled. The patient may also self-administer a first patch containing glutathione and a second patch containing a plurality of vitamins daily. In some instances, the patient may self-administer nitric oxide. The patient may also self-administer one or more posture improvement devices, such as a posture pillow wedge and/or a posture shoulder strap.

Once the initial treatment phase is complete, the maintenance phase may include a plurality of maintenance phase therapy sessions, which may be administered once every three months for a period of nine months. Each maintenance phase therapy session may include the same steps as an initial phase therapy session, but maintenance phase therapy sessions are administered farther apart in time than initial phase therapy sessions. During the maintenance phase, the patient may conduct maintenance phase personal administration, which may include an or all of the same stapes as an initial phase personal administration. For example, during a maintenance phase personal administration, the patient may at least self-administer the high frequency device. In some examples, the patient may conduct aa maintenance phase personal administration by applying the high frequency device to the scalp about once per week for a period of about five minutes at each occurrence. The patient may also periodically self-administer a first patch containing glutathione and a second patch containing a plurality of vitamins. In some instances, the patient may periodically self-administer nitric oxide. The patient may also periodically self-administer one or more posture improvement devices, such as a posture pillow wedge and/or a posture shoulder strap.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A regenerative treatment method for stimulating hair growth, the method comprising:

conducting an initial treatment phase comprising at least one initial phase therapy session and at least one initial phase personal administration that occurs after the at least one initial phase therapy session, wherein each initial phase therapy session includes at least subcutaneously applying carbon dioxide in at least one location on a scalp of a patient and each initial phase personal administration includes at least applying a high frequency ozone producing device to the scalp; and conducting a maintenance treatment phase after the initial treatment phase, the maintenance phase comprising at least one maintenance phase therapy session and at least one maintenance phase personal administration that occurs after the at least one maintenance phase therapy session, wherein each maintenance phase therapy session includes at least subcutaneously applying carbon dioxide in at least one location on the scalp of the patient and each maintenance phase personal administration includes at least applying a high frequency ozone producing device to the scalp.

2. The regenerative treatment method of claim 1, wherein each initial phase therapy session further comprises a step of:

administering a nitric oxide test to the patient prior to subcutaneously applying carbon dioxide; and orally administering nitric oxide when the patient is determined to have low levels of nitric oxide.

3. The regenerative treatment method of claim 1, wherein each initial phase therapy session and each maintenance phase therapy session further comprises:

applying suction to the scalp after the subcutaneously applying carbon dioxide.

4. The regenerative treatment method of claim 1, wherein each initial phase therapy session and each maintenance phase therapy session further includes:

conducting a secondary treatment of the scalp after the subcutaneously applying carbon dioxide, wherein the secondary treatment includes at least one of:

applying nutrients topically onto the scalp; and applying energy input to the scalp.

5. The regenerative treatment method of claim 4, wherein the secondary treatment comprises applying energy input to the scalp, and the applying energy input includes providing electrical current to the scalp using a high frequency ozone producing device that operates at 50 Hertz.

6. The regenerative treatment method of claim 4, wherein the secondary treatment comprises the applying energy input to the scalp, and the applying energy input includes providing near infrared light to the scalp.

7. The regenerative treatment method of claim 4, wherein the secondary treatment comprises the applying energy input to the scalp, and the applying energy input includes providing electromagnetic pulses using electromagnetic fields of from about 25 MHz to about 27 Mhz.

8. The regenerative treatment method of claim 4, wherein the secondary treatment comprises the applying nutrients topically onto the scalp.

9. The regenerative treatment method of claim 4, wherein the secondary treatment comprises the applying nutrients topically onto the scalp; and the applying energy input to the scalp includes applying a high frequency ozone producing device to the scalp.

10. The regenerative treatment method of claim 1, wherein the high frequency ozone producing device operates at 50 Hertz.

11. The regenerative treatment method of claim 1, wherein the high frequency ozone producing device is applied for a period of time that is at least about 5 minutes.

12. The regenerative treatment method of claim 1, wherein each initial phase personal administration further comprises:

administering a first patch to skin of a patient, the first patch including glutathione; and administering a second patch to the skin of the patient, the second patch comprising a plurality of vitamins.

13. A regenerative treatment kit for use during personal administration sessions of a regenerative treatment therapy to stimulate hair growth, the regenerative treatment kit comprising:

a high frequency ozone producing device;

a first patch configured to be applied to a patient's skin, the first patch including glutathione; and nitric oxide in a form to be taken orally.

14. The regenerative treatment kit of claim 13, further comprising a second patch configured to be applied to a patient's skin, the second patch including a plurality of vitamins.

15. The regenerative treatment kit of claim 13, wherein the regenerative treatment kit comprises a plurality of first patches, each first patch including glutathione, and a plurality of second patches, each second patch including a plurality of vitamins.

16. The regenerative treatment kit of claim 13, wherein the high frequency ozone producing device is configured to operate at 50 hertz.

17. The regenerative treatment kit of claim 13, further comprising a posture shoulder strap.

18. The regenerative treatment kit of claim 13, further comprising a posture wedge pillow.

19. A regenerative treatment method for stimulating hair growth, the method comprising:

conducting an initial treatment phase comprising a plurality of initial phase therapy sessions and a plurality of initial phase personal administrations, wherein at least one of the plurality of initial phase personal administrations occurs after at least one of the plurality of initial phase therapy sessions;

wherein each initial phase therapy session includes at least subcutaneously applying carbon dioxide in at least one location on a scalp of a patient and each initial phase personal administration includes at least applying a high frequency ozone producing device to the scalp;

wherein the plurality of initial phase therapy sessions includes from ten to twenty initial therapy sessions, and one of the plurality of initial phase therapy sessions occurs once every seven to ten days; and conducting a maintenance treatment phase after the initial treatment phase, the maintenance phase comprising a plurality of maintenance phase therapy sessions and a plurality of maintenance phase personal administrations, wherein at least one of the plurality of maintenance phase personal administrations occurs after at least one of the plurality of maintenance phase therapy sessions;

wherein each maintenance phase therapy session includes at least subcutaneously applying carbon dioxide in at least one location on the scalp of the patient and each maintenance phase personal administration includes at least applying a high frequency ozone producing device to the scalp; and wherein occurrence of each one of the plurality of maintenance phase therapy sessions is spaced apart over a greater period of time than each one of the initial phase therapy sessions.

20. The regenerative treatment method of claim 19, wherein:

applying a high frequency ozone producing device to the scalp during one of the plurality of initial phase personal administrations occurs daily during the initial phase for a time period of three to ten minutes; and applying a high frequency ozone producing device to the scalp during one of the plurality of maintenance phase personal administrations occurs once per week during the maintenance phase for a time period of three to ten minutes.

* * * * *